United States Patent [19]

Cooper et al.

[11] 4,048,430
[45] Sept. 13, 1977

[54] MERCAPTOPSEUDOTRISACCHARIDES

[75] Inventors: David J. Cooper, Downingtown; John R. E. Hoover, Glenside, both of Pa.; Jerry A. Weisbach, Cherry Hill, N.J.

[73] Assignee: SmithKline Corporation, Philadelphia, Pa.

[21] Appl. No.: 642,085

[22] Filed: Dec. 18, 1975

Related U.S. Application Data

[63] Continuation-in-part of Ser. No. 518,428, Oct. 29, 1974, Pat. No. 3,960,838.

[51] Int. Cl.$^2$ ............................................. C07H 15/22
[52] U.S. Cl. .................................... 536/17; 424/180; 536/4
[58] Field of Search ................... 260/210 AB, 210 K; 536/4, 17

[56] References Cited

U.S. PATENT DOCUMENTS

| 3,753,973 | 8/1973 | Umezawa et al. | 260/210 K |
| 3,886,138 | 5/1975 | Naito et al. | 260/210 K |

Primary Examiner—Johnnie R. Brown
Attorney, Agent, or Firm—Stuart R. Suter; William H. Edgerton; Alan D. Lourie

[57] ABSTRACT

Novel pseudodisaccharide compounds which are related to neamine are prepared. These compounds have a mercapto group or a derivative thereof at position 3 or 4 of the glucose moiety of neamine. The compounds have antibacterial activity and have utility as intermediates to pseudotrisaccharides.

12 Claims, No Drawings

MERCAPTOPSEUDOTRISACCHARIDES

This application is a continuation-in-part of copending application Ser. No. 518,428, filed Oct. 29, 1974 now Pat. No. 3,960,838.

This invention relates to novel pseudodisaccharides comprised of 2-deoxystreptamine or a derivative thereof and a hexose moiety and to novel pseudotrisaccharides obtained therefrom. In particular, the sugar moieties are 3- or 4-deoxy-3- or 4-mercapto-2,6-diaminopyranose derivatives. The compounds exhibit antibacterial activity and are useful as chemical intermediates to prepare compounds which are antibacterial agents.

BACKGROUND

Aminoglycosides are an important group of antibiotics of which the commercial members are prepared by fermentation methods. Many aminoglycosides have as part of their structure the pseudodisaccharide neamine which has the following structure:

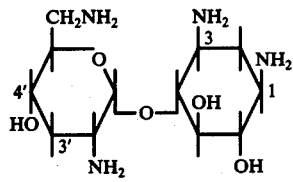

The systematic name is 2-deoxy-4-O-(2,6-diamino-2,6-dideoxy-α-D-glucopyranosyl)-D-streptamine. Compounds in which the neamine structure has been modified are known in nature. These modifications are limited to absence of the 3'-hydroxy, the 4'-hydroxy or both the 3'- and 4'-hydroxy groups. Tobramycin, 4'deoxybutirisin A and B, and gentamicin are examples of aminoglycosides containing these modified neamines. Antibiotics containing neamines with substituents other than hydrogen or hydroxy at the 3' or 4' positions have not been reported either from fermentation or chemical modification methods.

Aminoglycosides also exist in nature as pseudotrisaccharides. For example, kanamycin are known antibiotics which are described in the Merck Index, 8th ed., pp. 597-598. Kanamycin B is a compound with the following structure:

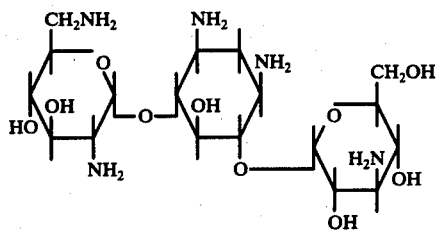

Kanamycins lacking the 3' and 4'-hydroxy groups are also known; however, kanamycins with sulfur substituents at the 3' or 4' positions are not known.

SUMMARY OF THE INVENTION

The compounds of this invention are represented by the following structure:

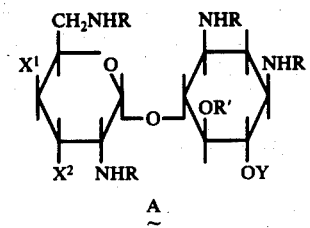

A or

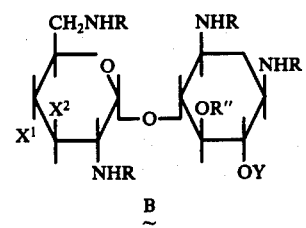

B where
$X^1$ and $X^2$ are each $SR''$ or $OR'$ but are not the same;
R is hydrogen or an amino protecting group;
R' is hydrogen or a hydroxy protecting group;
R" is hydrogen or a mercapto protecting group; and
Y is R', 3-amino-3-deoxy-D-glucopyranosyl, 3-acetamido-3-deoxy-D-glucopyranosyl, 3-acetamido-3-deoxy-2,4,6-O-triacetyl-D-glucopyranosyl, or 3-acetamide-3-deoxy-2,4,6-O-tribenzyl-D-pyranosyl.

The above structures indicate that $X^1$ and $X^2$ may be axially or equatorially oriented; however, the compounds of this invention have the X substituents in only an axial-axial or equatorial-equatorial orientation. When the X-substituents have axial-axial orientation the diaminosugar has the gulo configuration. When the X-substituents have equatorial-equatorial orientation the diaminosugar has the gluco configuration and the compound is a modified neamine.

The amino protecting group is any group used in the arts of carbohydrate or peptide synthesis to protect amino groups during chemical reactions and is subsequently removed to obtain the free amino group; for example, acetyl, tosyl, benzoyl, mesyl, methylsulfate, dichloroacetyl, trichloroethoxycarbonyl, benzyloxycarbonyl, t-butoxycarbonyl, ethoxycarbonyl, methoxycarbonyl, dinitrophenyl, enamine adduct of dimedone and the like. Hydroxy protecting groups which are known and used in the art in a manner like the amino protecting groups include, in addition to most of the amino protecting groups, benzyl, trityl, methyl, tetrahydropyranyl, cyclohexylidene, isopropylidene, trifluoroacetyl, nitrate, methylene, carbonyl and other groups used in the carbohydrate art. Preferred amino protecting groups are benzyloxycarbonyl, t-butoxycarbonyl, ethoxycarbonyl, methoxycarbonyl and dinitrophenyl. Preferred hydroxy protecting groups are acetyl, benzoyl, dichloroacetyl, trichloroethoxycarbonyl and cyclohexylidene. The choice of the protecting group depends on various factors including whether an amino or hydroxy group is being protected, subsequent reaction conditions, and conditions for removal. The choice of the proper protecting group is within the ordinary ability of one skilled in the art.

The pseudodisaccharide compounds of this invention are prepared by reacting a sulfur nucleophile with a 3',4'-allo-anhydroneamine (4) or 3',4'-galacto-anhydroneamine (1) as outlined in Scheme I and II.

When the galacto-epoxide isomer is reacted as in Scheme I two isomers are obtained, the 3'-hydroxy-4'-mercapto derivative in a gluco configuration and the 4'-hydroxy-3'-mercapto derivative in the gulo configuration. Likewise, the 3'-hydroxy-4'-mercapto derivative in the gulo configuration and the 4'-hydroxy-3'-mercapto derivative in the gluco configuration are obtained when the allo-epoxide isomer is reacted as outlined in Scheme II. In both cases, the mixture of isomers can be separated by standard methods such as column chromatography or other chromatographic methods in each individual isomer. Removal of the protecting groups by standard methods gives each isomer where R, R', and R'' are each hydrogen.

Typical sulfur nucleophiles which can be used in Schemes I and II are thiocyanate ion, thiolacetate ion, thiolbenzoate ion or a salt of benzyl mercaptan, p-methoxybenzyl mercaptan, p-chlorobenzyl mercaptan or trityl mercaptan, and the like. These nucleophiles give compounds where R'' is cyano, acetyl, benzoyl, benzyl, p-methoxybenzyl, p-chlorobenzyl, trityl and the like. Base or acid hydrolysis or reduction of these compounds by known methods give the compounds where R'' is hydrogen.

More specifically, when the 3',4'-galactoepoxide of neamine with the amino and hydroxy groups protected is reacted with the sodium salt of benzyl (2,6-diamino-3-mercapto-2,3,6-trideoxy-α-D-glucopyranosyl)-D-streptamine (5 where R, R', and R'' are hydrogen) and 2-deoxy-4-O-(2,6-diamino-4-mercapto-2,4,6-trideoxy-α-D-gulopyranosyl)-D-streptamine (6 when R, R' and R'' are hydrogen).

The pseudotrisaccharide compounds of this invention are prepared by reacting the pseudodisaccharides, which are suitably protected, with 3-amino-3-deoxy-α-D-glucopyranosyl chloride in which the amino and hydroxy groups are suitably protected. For example, 2-deoxy-4-O-(2,6-dimethoxycarbonylamino-3-O-acetyl-4-benzylmercapto-2,4,6-trideoxy-α-D-glucopyranosyl)-1,3-N-dimethoxycarbonyl-D-streptamine is condensed with 3-acetamido-2,4,6-tri-O-benzyl-3-deoxy-α-D-glucopyranosyl chloride [*Agr. Biol. Chem.*, 32, 1123 (1968)] by standard processes for preparing kanamycin B [*J. Antibiotics*, 21, 424 (1968)] to give 2-deoxy-4-O-(2,6-dimethoxycarbonylamino-3-O-acetyl-4-benzylmercapto-2,4,6-trideoxy-α-D-glucopyranosyl)-6-O-(3-acetamido-2,4,6-tri-O-benzyl-3-deoxy-α-D-glucopyranosyl)-1,3-N-dimethoxycarbonyl-D-streptamine. Removal of the protecting groups gives the pseudotrisaccharide to which the trivial name of 4'-mercapto-4'-deoxykanamycin B can be given. The mercaptopseudodisaccharide compounds of this invention can be condensed with the 3-aminoglucose derivative by this process or other known α-glucosylation processes to give useful pseudotrisaccharides.

Compounds of this invention where R, R', R'' and Y

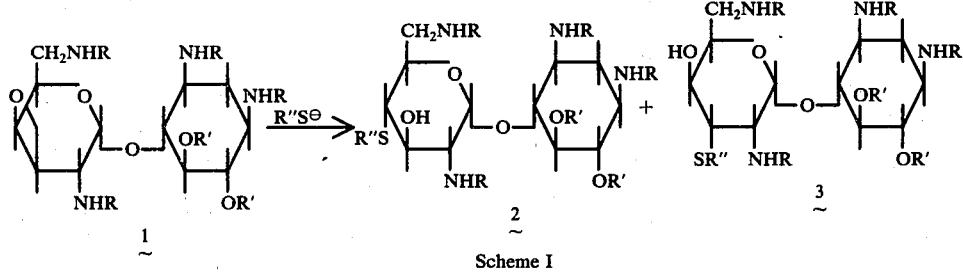

Scheme I

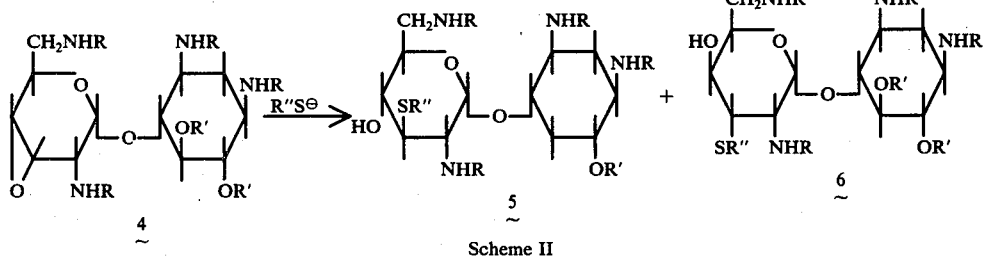

Scheme II mercaptan the product obtained is a mixture of the gluco-4'-benzylmercapto (2) and the gulo-3'benzylmercapto derivatives (3). Column chromatography on silica gel separates the product into the two isomers. Removal of the protecting groups gives 2-deoxy-4-O-(2,6-diamino-4-mercapto-2,4,6-trideoxy-α-D-glucopyranosyl)-D-streptamine (2 where R, R', and R'' are hydrogen) and 2-deoxy-4-O-(2,6-diamino-3-mercapto-2,3,6-trideoxy-α-D-gulopyranosyl)-D-streptamine (3 where R, R', and R'' are hydrogen).

Similarly, reaction of the 3',4'-allo-epoxide of neamine, which has the amino and hydroxy groups protected, with sodium benzyl mercaptan gives a mixture of the gulo-4'-benzylmercapto (6) and the gluco-3'-benzylmercapto (5) derivatives. Column chromatography on silica gel separates this mixture into each isomer. Removal of the protecting groups gives 2-deoxy-4-O- are hydrogen have antibacterial activity against a variety of bacteria and are especially active against Pseudomonas. Minimum inhibitory concentrations (MIC), as obtained in a standard agar inclusion test screen, range from 25 to 200 μg/ml against *Pseudomonas aeruginosa*. For example, 2-deoxy-4-O-(2,6-diamino-4-mercapto-2,4,6-trideoxy-α-D-glucopyranosyl)-D-streptamine gave a MIC of 25 μg/ml against the Pseudomonas species while 2-deoxy-4-O-(2,6-diamino-3-mercapto-2,3,6-trideoxy-α-D-glucopyranosyl)-D-streptamine gave a MIC of 63 μg/ml against Pseudomonas, In contrast, neamine gave an MIC of greater than 200 μg/ml in the same test against Pseudomonas.

Compounds of this invention where R, R', R'' and Y are protecting groups generally exhibit little or no antibacterial activity; however, these compounds are useful in the preparation of the compounds where R, R' and R" are hydrogen or in the preparation of the new modified pseudotrisaccharides of this invention which are antibacterial agents.

Compounds of this invention where R, R' and R" are hydrogen and Y is 3-amino-3-deoxy-α-D-glucopyranosyl have antibacterial activity. For example, 4'-mercapto-4'deoxykanamycin B gave MIC values ranging from 6.3 to >200 μg/ml in an in vitro screen against various Gram-positive and Gram-negative bacteria. The compound was active against Pseudomonas at 25 μg/ml.

The compounds with antibacterial activity can be used in aqueous solutions to sterilize glassware; instruments and the like. In addition, they may be formulated into injectable pharmaceutical compositions in a similar manner as other known aminoglycoside compounds and used to prevent or treat bacteria infections.

The following examples illustrate the invention but are not to be construed as limiting the scope thereof.

PREPARATION 1

To a stirred solution of 5,6-O-cyclohexylidenetetra-N-methoxycarbonylneamine (50.0 g, 0.078 mol) in dry pyridine (150 ml) and freshly distilled chloroform (100 ml) is added dropwise over a 6 hour period at room temperature a solution of p-toluenesulfonyl chloride (25.6 g, 0.134 mol) in chloroform (70 ml). The reaction is stirred overnight, diluted with ice cold brine and extracted with ethyl acetate. The extracts are washed with brine, 10% acetic acid (until pH <7) and saturated $NaHCO_3$ (until pH >7). The dried extracts are evaporated to give the 3'-tosyl-4'-hydroxy derivative which is chromatographed on a silica gel column using chloroform and methanol (1–3%) in chloroform as eluant.

The product (4.3 g, 5.45 mmol) is dissolved in chloroform (60 ml), cooled in an ice bath and then treated with a solution of sodium (0.5 g, 21.8 mmol) in dry methanol (15 ml). After 28 hours at 5°–10° C the reaction is diluted with cold brine (25 ml) and partitioned with ethyl acetate. The organic phase is washed with brine, dried, and evaporated to a solid which is recrystallized from acetone-ether to give 3',4'-allo-anhydro-5,6-O-cyclohexylidene-tetra-N-methoxycarbonylneamine; $[\alpha]_D^{25} - 8.8$ (c 1, $CHCl_3$).

PREPARATION 2

Benzoyl chloride (53.7 g, 0.38 mol) is added dropwise to a solution of 5,6-O-cyclohexylidene-tetra-N-methoxycarbonylneamine (106.5 g, 0.168 mol) in pyridine (600 ml) at $-11°$ C ± 1°. Water (100 ml) is added and then saturated $NaHCO_3$ until pH 7–8 is obtained. The solution is extracted with ethyl acetate which is dried and concentrated in vacuo to give a residue which is evaporated with toluene and triturated with ether. The solid is recrystallized from ethyl acetate to give the 3'-benzoyl-4'-hydroxy derivative; $[\alpha]_D^{25} + 67.4$ (c 1% MeOH).

A solution of the above product (27.5 g, 0.0373 mol) and triethylamine (15.1 g, 0.149 mol) in a mixture of chloroform (350 ml) and tetrahydrofuran (120 ml) is treated dropwise at $-10°$ C with mesyl chloride (11 g, 0.095 mol). The solution is diluted with saturated $NaHCO_3$ (400 ml) at about 0° and then extracted with chloroform. The dried extracts are evaporated in vacuo to a residue which is reprecipitated from chloroform-petroleum ether to give the 3'-benzoyl-4'-mesyl compound; $[\alpha]_D^{25} + 32.5$ (c 1, $CHCl_3$).

A solution of sodium (16.1 g, 0.7 mol) in methanol (500 ml) is added at room temperature to a solution of the 3'-benzoyl-4'-mesyl compound (80 g, 0.098 mol). After 1 hour solid $NaHCO_3$ and then glacial acetic acid (30 ml) are added. The resulting solution (pH ~7) is evaporated to give a residue which is partitioned between chloroform and water. The aqueous phase is separated and extracted with chloroform. The combined chloroform phases are washed with water, dried and concentrated to a residue which is dissolved in methylene chloride (400 ml) and added with stirring to petroleum ether (4 l). The solid 3',40'-galacto-anhydro-5,6-O-cyclohexylidene-tetra-N-methoxycarbonylneamine (49 g) is collected by filtration and dried in vacuo; $[\alpha]_D^{25} + 2.5$ (c 1, $CHCl_3$).

EXAMPLE 1

To a solution of sodium (1.10 g, 48.6 mmol) dissolved in methanol (20 ml) under a nitrogen atmosphere is added at room temperature benzyl mercaptan (5.8 ml, 48.6 mmol). To this solution is added the epoxide of Preparation 2 (15.0 g, 24.3 mmol) and the reaction is heated at 60° C for 2 hours. The solution is cooled, adjusted to pH 7 and poured into ice water (500 ml). The product which precipitated is taken up in ethyl acetate. The dried solution is evaporated to give a white solid which is a mixture of isomers. The solid is triturated with boiling benzene (200 ml) which on cooling gave 2-deoxy-4-O-(2,6-dimethoxycarbonylamino-4-benzylmercapto-2,4,6-trideoxy-α-D-glucopyranosyl)-1,3-N-dimethoxycarbonyl-5,6-cyclohexylidene-D-streptamine (isomer 1) (8.4 g) m.p. 208°–9° C. The benzene filtrate is evaporated to give 2-deoxy-4-O-(2,6-dimethoxycarbonylamino-3-benzylmercapto-2,3,6-trideoxy-α-D-gulopyranosyl)-1,3-N-dimethoxycarbonyl-5,6-cyclohexylidene-D-streptamine (isomer 2), contaminated with isomer 1. Isomers are separated by column chromatography on silica gel with 1.2% methanol in chloroform as eluant.

EXAMPLE 2

Isomer 1 from Example 1 (9.5 g, 12.7 mmol) is stirred in methanol (150 ml) containing 3N HCl (15 ml) for 3.5 hours at room temperature. The solution is neutralized with saturated $Ba(OH)_2$ and the methanol is removed in vacuo at 40° C. The residue is azeotroped with two 80 ml portions of ethanol and then triturated with 1:1 ether:petroleum ether to give 2-deoxy-4-O-(2,6-dimethoxycarbonylamino-4-benzylmercapto-2,4,6-trideoxy-α-D-glucopyranosyl)-1,3-N-dimethoxycarbonyl-D-streptamine.

The above product (8.4 g, 12.7 mmol) is refluxed for 20 hours in a solution of $Ba(OH)_2 \cdot 8 H_2O$ (40 g, 0.127 mol) in water (50 ml) and methanol (20 ml) and then saturated with $CO_2$. The $BaCO_3$ is collected and washed with hot water and a mixture of methanol and water. The filtrate and washings are concentrated to a residue which is taken up in water and acidified with 2N $H_2SO_4$. The $BaSO_4$ is removed and the filtrate is concentrated to a small volume which is placed on a column of polymethacrylic acid ion exchange resin in ammonium form [Amberlite IRC-50 ($NH_4^+$)]. The product, 2-deoxy-4-O-(2,6-diamino-4-benzylmercapto-2,4,6-trideoxy-α-D-glucopyranosyl)-D-streptamine, is eluted with a 0.066N to 0.3N $NH_4OH$ gradient followed by 0.3N and 1N $NH_4OH$. The sulfate salt is prepared by standard methods; $[\alpha]_D^{25} + 104.2$ (c 1, $H_2O$).

The above free base product (458 mg, 1.07 mmol) is treated with liquid ammonia (45 ml) containing sodium (59.2 mg, 2.57 mmol) under a nitrogen atmosphere for 1 hour. The solvent is removed and the residue is acidified with 0.1N $H_2SO_4$ (50 ml) and lyophilized to give 2-deoxy-4-O-(2,6-diamino-4-mercapto-2,4,6-trideoxy-α-D-glucopyranosyl)-D-streptamine as the sulfate salt; $[\alpha]_D^{25} + 42.5$ (c 1, $H_2O$).

EXAMPLE 3

Isomer 2 from Example 1 is deblocked by treatment with acid and then base according to the procedure of Example 2 to give 2-deoxy-4-O-(2,6-diamino-3-benzyl-mercapto-2,3,6-trideoxy-α-D-gulopyranosyl)-D-streptamine. The sulfate salt is prepared by standard methods; $[\alpha]_D^{25} + 34$ (c 1, $H_2O$).

Treatment of this product with sodium in liquid ammonia by the procedure in Example 2 gives 2-deoxy-4-O-(2,6-diamino-3-mercapto-2,3,6-trideoxy-α-D-gulopyranosyl)-D-streptamine as its sulfate salt, $[\alpha]_D^{25} + 34$ (c 0.5, $H_2O$).

EXAMPLE 4

When the epoxide from Preparation 1 is reacted with the sodium salt of benzyl mercaptan by the procedure of Example 1, a mixture of two isomers is obtained, 2-deoxy-4-O-(2,6-dimethoxycarbonylamino-3-benzylmercapto-2,3,6-trideoxy-α-D-glucopyranosyl)-1,3-N-dimethoxycarbonyl-5,6-cyclohexylidene-D-streptamine (isomer 3) and 2-deoxy-4-O-(2,6-dimethoxycarbonylamino-4-benzylmercapto-2,4,6-trideoxy-α-D-gulopyranosyl)-1,3-N-dimethoxycarbonyl-5,6-cyclohexylidene-D-streptamine (isomer 4). The mixture is chromatographed on a silica gel column with 1:1 ethyl acetate: cyclohexane as eluant to separate the isomers. Isomer 3, $[\alpha]_D^{25} + 25$ (c 1, $CHCl_3$). Isomer 4, $[\alpha]_D^{25} - 82$ (c 1, $CHCl_3$).

EXAMPLE 5

Treatment of isomer 3 from Example 4 with HCl and then $Ba(OH)_2$ according to the procedure of Example 2 gives 2-deoxy-4-O-(2,6-diamino-3-benzylmercapto-2,3,6-trideoxy-α-D-glucopyranosyl)-D-streptamine; sulfate salt $[\alpha]_D^{25} + 76$ (c 1, $H_2O$). Reaction of this product with sodium in liquid ammonia by the procedure in Example 2 gives 2-deoxy-4-O-(2,6-diamino-3-mercapto-2,3,6-trideoxy-α-D-glucopyranosyl)-D-streptamine; sulfate salt $[\alpha]_D^{25} + 53$ (c 1, $H_2O$).

EXAMPLE 6

Isomer 4 from Example 4 is treated with HCl and $Ba(OH)_2$ by the procedures described in Example 2 to give 2-deoxy-4-O-(2,6-diamino-4-benzylmercapto-2,4,6-trideoxy-α-D-gulopyranosyl)-D-streptamine; sulfate salt $[\alpha]_D^{25} + 44.9$ (c 1, $H_2O$). The benzyl group was removed from this product by the sodium in liquid ammonia procedure in Example 2 to give 2-deoxy-4-O-(2,6-diamino-4-mercapto-2,4,6-trideoxy-α-D-gulopyranosyl)-D-streptamine as its sulfate salt; $[\alpha]_D^{25} + 57.2$ (c 1, $H_2O$).

EXAMPLE 7

2-Deoxy-4-O-(2,6-dimethoxycarbonylamino-4-benzylmercapto-2,4,6-trideoxy-α-D-glucopyranosyl)-1,3-N-dimethoxycarbonyl-5,6-cyclohexylidene-D-streptamine (24.5 g, 0.033 mol) is dissolved in pyridine (100 ml) and acetic anhydride (80 ml) and stirred at room temperature for 18 hours. The reaction solution is evaporated in vacuo at 35° and the residue is dissolved in methylene chloride and precipitated by the addition of petroleum ether to give the solid 3'-acetoxy derivative (21 g).

The above product is dissolved in methanol (150 ml) and 3N HCl (10 ml). After four hours the neutralized reaction mixture is evaporated and the residue is partitioned between water and ethyl acetate. The aqueous layer is extracted with ethyl acetate. The combined ethyl acetate solutions are dried and evaporated to give the 5,6-dihydroxy derivative which is reprecipitated from isopropanol-ether.

A mixture of the above diol (7 g, 10 mmol), silver carbonate (9.5 g), dry silver perchlorate (250 mg), calcium sulfate (70 g), absolute chloroform (110 ml) and peroxide-free dioxane (35 ml) is protected from light and moisture and stirred overnight. To the mixture is added 3-acetamido-2,4,6-tri-O-benzyl-3-deoxy-α-D-glucopyranosyl chloride (3.5 g, 7 mmol). The reaction is stirred 6 days, quenched with methanol (20 ml), stirred one hour, and filtered through filter-aid. The solids are washed with methylene chloride. The combined filtrate and washings are washed with saturated $NaHCO_3$ and saturated NaCl, dried and concentrated to an oil. The oil is dissolved in methylene chloride (25 ml) and added dropwise to a 2:1 mixture of ether: petroleum ether (600 ml). The product (8 g) is chromatographed on silica gel (800 g) with toluene-methanol as eluant to give a mixture of trisaccharides (1.5 g). The mixture is resolved into four components by further chromatography on silica gel with 1:1 acetone-hexane as eluant. Tlc analysis on silica gel with 1:1 acetone-hexane gave $R_f$ values of 0.26 (48 mg), 0.19 (35 mg), 0.16 and 0.13 for the components. $R_f$ 0.16 component: 145 mg, mp 252°–255°, $[\alpha]_D + 33.2$ (c 0.5, $CHCl_3$); $R_f$ 0.13 component: 650 mg, mp 138°–145° d, $[\alpha]_D^{25} + 62.7$ (c 0.5, $CHCl_3$).

The $R_f$ 0.13 component (250 mg, 0.213 mmol) is dissolved in liquid ammonia (25 ml) and is treated under nitrogen with sodium until the blue color remained 30 minutes (50 mg). The suspension is clarified with methanol (5 ml) and treated with benzyl chloride (60 mg). After 30 minutes the cold solution is quenched with saturated $NaHCO_3$ (10 ml), filtered and concentrated. The solid residue is stirred with methanol, the solution is filtered, and the filtrate is evaporated in vacuo to give 2-deoxy-4-O-(2,6-dimethoxycarbonylamino-4-benzylmercapto-2,4,6-trideoxy-α-D-glucopyranosyl)-6-O-(3-acetamido-3-deoxy-α-D-glucopyranosyl)-1,3-N-dimethoxycarbonyl-D-streptamine.

The above product is treated overnight with acetic anhydride and pyridine. The reaction is filtered and evaporated to give a residue which is partitioned between methylene chloride and $NaHCO_3$ solution. The dried organic phase is concentrated to give the peracetylated derivative which is precipitated from 1:1 ether-petroleum ether. $[\alpha]_D$ 84.7° (c 0.5, $CHCl_3$).

The above product (135 mg) is dissolved in a water (5 ml) and methanol (5 ml) mixture which contained barium hydroxide hydrate (1.5 g). The reaction is refluxed overnight, neutralized with $CO_2$ at 100°, and filtered. The solid is washed with boiling water. The filtrates are concentrated to 10 ml, cooled and acidified with dilute $H_2SO_4$. The $BaSO_4$ is removed by filtration and washed. The combined filtrate and washings are neutralized with ion-exchange resin [Amberlite IRA-400(OH)] and then lyophilized to give a mixture of 4'-benzylmercapto-4'-deoxykanomycin B and an internal cylic urea derivative. This mixture is heated overnight in a steel bomb at 150° with n-butyl amine. The solution is concentrated and the residue is dissolved in water (25 ml)

and extracted with methylene chloride. The aqueous phase is lyophilized to give 4'-benzylmercapto-4'-deoxykanomycin B (50 mg).

The above product (40 mg) is dissolved in liquid ammonia (10 ml) and treated under nitrogen with sodium (5 mg). The reaction is quenched with degassed water (3 ml) and the suspension is filtered, concentrated and lyophilized to remove ammonia. The residue is dissolved in water (10 ml), adjusted to pH 6 with dilute H$_2$SO$_4$ and lyophilyzed to give 4'-deoxy-4'-mercaptokanamycin B; [α]$_D$ 65.6° (c 0.2, H$_2$O).

The other trisaccharide components isolated above are deblocked in a similar manner as outlined above to give the corresponding products. The R$_f$ 0.16 component is deblocked as described above to give 2-deoxy-4-O-(2,6-diamino-4-mercapto-2,4,6-trideoxy-α-D-glucopyranosyl)-6-O-(3-amino-3-deoxy-β-D-glucopyranosyl)-D-streptamine.

We claim:
1. A compound of the formula

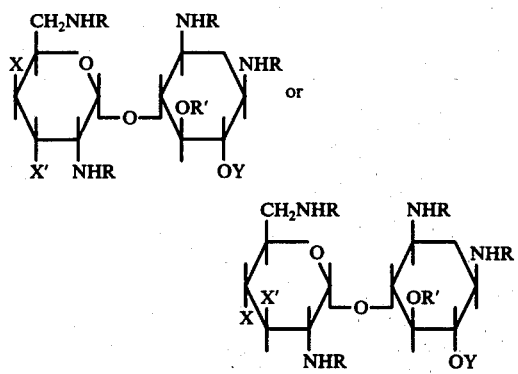

where
X and X' are each SR" or OR' but are not the same;
each R is hydrogen or an amino protecting group;
each R' is hydrogen or a hydroxy protecting group;
R" is hydrogen or a mercapto protecting group; and
Y is 3-amino-3-deoxy-D-glucopyranosyl, 3-acetamido-3-deoxy-D-glucopyranosyl, 3-acetamido-3-deoxy-2,4,6-O-triacetyl-D-glucopyranosyl, or 3-acetamido-3-deoxy-2,4,6-O-tribenzyl-D-glucopyranosyl.

2. A compound as claimed in claim 1 where R is hydrogen, acetyl, tosyl, benzoyl, mesyl, methylsulfate, dichloroacetyl, trichloroethoxycarbonyl, benzyloxycarbonyl, t-butoxycarbonyl, ethoxycarbonyl, methoxycarbonyl, dinitrophenyl or dimedone adduct; R' is hydrogen, acetyl, tosyl, benzoyl, mesyl, methylsulfonate, dichloroacetyl, trichloroethoxycarbonyl, benzyloxycarbonyl, t-butoxycarbonyl, ethoxycarbonyl, methoxycarbonyl, benzyl, trityl, methyl, tetrahydropyranyl, trifluoroacetyl, nitro or, when taken together with another R', cyclohexylidene, isopropylidene, methylene, or carbonyl; and R" is hydrogen, benzyl, p-methoxybenzyl, p-chlorobenzyl, acetyl, benzoyl, cyano or triphenylmethyl.

3. A compound as claimed in claim 2 where the compound has structural formula A.

4. A compound as claimed in claim 2 where the compound has structural formula B.

5. A compound as claimed in claim 4 where X is SR" and X' is OR'.

6. A compound as claimed in claim 5 being the compound 2-deoxy-4-O-(2,6-dimethoxycarbonylamino-4-benzylmercapto-2,4,6-trideoxy-3-acetyl-α-D-glucopyranosyl)-6-O-(3-acetamido-3-deoxy-α-D-glucopyranosyl)-1,3-N-dimethoxycarbonyl-D-streptamine.

7. A compound as claimed in claim 5 being the compound 2-deoxy-4-O-(2,6-dimethoxycarbonylamino-3-O-acetyl-4-benzylmercapto-2,4,6-trideoxy-α-D-glucopyranosyl)-6-O-(3-acetamido-3-deoxy-2,4,6-O-triacetyl-α-D-glucopyranosyl)-1,3-N-dimethoxycarbonyl-D-streptamine.

8. A compound as claimed in claim 5 being the compound 2-deoxy-4-O-(2,6-diamino-4-benzylmercapto-2,4,6-trideoxy-α-D-glucopyranosyl)-6-O-(3-amino-3-deoxy-α-D-glucopyranosyl)-D-streptamine.

9. A compound as claimed in claim 5 being the compound 2-deoxy-4-O-(2,6-diamino-4-mercapto-2,4,6-trideoxy-α-D-glucopyranosyl)-6-O-(3-amino-3-deoxy-α-D-glucopyranosyl)-D-streptamine.

10. A compound as claimed in claim 5 being the compound 2-deoxy-(2,6-dimethoxycarbonylamino-4-benzylmercapto-3-O-acetyl-2,4,6-trideoxy-α-D-glucopyranosyl)-6-O-(3-acetamido-3-deoxy-β-D-glucopyranosyl)-1,3-N-dimethoxycarbonyl-D-streptamine.

11. A compound as claimed in claim 5 being the compound 2-deoxy-4-O-(2,6-diamino-4-mercapto-2,4,6-trideoxy-α-D-glucopyranosyl)-6-O-(3-amino-3-deoxy-β-D-glucopyranosyl)-D-streptamine.

12. A compound as claimed in claim 5 being the compound 2-deoxy-4-O-(3-O-acetyl-2,6-dimethoxycarbonylamino-4-benzylmercapto-2,4,6-trideoxy-α-D-glucopyranosyl)-6-O-(3-acetamido-3-deoxy-2,4,6-O-tribenzyl-α-D-glucopyranosyl)-1,3-N-dimethoxycarbonyl-D-streptamine.

* * * * *